United States Patent [19]

Barbaric et al.

[11] Patent Number: 4,763,345
[45] Date of Patent: Aug. 9, 1988

[54] SLIT SCANNING AND DETECHING SYSTEM

[75] Inventors: Zoran L. Barbaric, Malibu; Michael Deckard, Sunland; Robert S. Nelson, Santa Monica, all of Calif.

[73] Assignee: The Regents of the University of California, Berkeley, Calif.

[21] Appl. No.: 882,093

[22] Filed: Jul. 3, 1986

Related U.S. Application Data

[63] Continuation-in-part of Ser. No. 636,238, Jul. 31, 1984.

[51] Int. Cl.⁴ .............................................. G21K 5/10
[52] U.S. Cl. .................................... 378/146; 378/145
[58] Field of Search .................. 378/15, 145–146, 378/198

[56] References Cited

U.S. PATENT DOCUMENTS

| | | | |
|---|---|---|---|
| 2,730,566 | 1/1956 | Bartow et al. | 378/146 |
| 4,179,100 | 12/1979 | Sashin et al. | 378/146 |
| 4,398,302 | 8/1983 | Pfeiler | 378/146 |
| 4,403,338 | 9/1983 | Rudin et al. | 378/146 |
| 4,541,107 | 9/1985 | Rossi | 378/146 |
| 4,581,753 | 4/1986 | Rice | 378/146 |
| 4,686,695 | 8/1987 | Macovski | 378/146 |

FOREIGN PATENT DOCUMENTS 1074211 1/1960 Fed. Rep. of Germany ...... 378/198

OTHER PUBLICATIONS

"Improved Contrast . . . Aperture Wheel Device", by Rudin et al., Radiology, vol. 137, #2, 11–1980.

*Primary Examiner*—Craig E. Church
*Assistant Examiner*—John C. Freeman
*Attorney, Agent, or Firm*—Poms, Smith, Lande & Rose

[57] ABSTRACT

A scanning system for use in radiology incorporates two disks bearing identically patterned, radial arrays of apertures and corresponding X-ray detection materials, respectively. The disks are axially aligned and synchronously rotated on opposite sides of the radiological target. X-rays emitted adjacent to the first disk are strobed by the apertures and detected by photodiode arrays on the second disk after passing through said target. The detection array is scanned to produce the X-ray information for digital processing and imaging. The foregoing apparatus may be portable and mounted for retrofitting relative to existing X-ray installations.

20 Claims, 2 Drawing Sheets

SLIT SCANNING AND DETECHING SYSTEM

This is a continuation-in-part of application Ser. No. 06/636,238 filed July 31, 1984.

FIELD OF THE INVENTION

The present invention relates to slit scanning and detecting systems and, more particularly, to X-ray projection and detection using slit scanning techniques for imaging the radiographic target under scrutiny.

BACKGROUND OF THE INVENTION

Modern advances in digital information and data processing technology have made it scientifically and economically feasible to extend digital imaging techniques into a broader range of radiographic applications. In particular, digital radiographic imaging has developed into an accepted modality for many X-ray applications, such as angiography.

It is known, for example, to couple Vidicon or Isocon cameras to a fluorescent X-ray screen and digitize the analog output of the camera. Among other advantages over conventional intensifying screen and film methods, digital processing techniques have helped reduce patient risk by reducing patient dosage due to greater detection efficiency of the X-ray receptors, by using the greater dynamic range of image intensifier camera units to reduce the amounts of contrast material, and by allowing image post-processing to remove overlying structures or distracting background (viz., subtraction techniques). However, these systems, because of their inherent slow reaction time have problems such as image misrepresentation due to patient motion between frames.

Digital linear slit scanning units for chest radiographic applications are known in the art. These units are generally dedicated devices consisting of an X-ray tube, a slit aperture, and photodiode detector elements. Low dose, single beam, spot scanning systems are also known and available on a commercial basis.

Also known in the prior art are multiple slit rotating disk systems for scatter reduction in film-based radiography. More recently, a scanning system has been described which would consist of a rotating, multiple-slit, cone-shaped X-ray aperture mechanism co-ordinated with a rotating cone having linear photodiode arrays mounted thereon as detectors. Such a system may provide greater scan uniformity and higher scan rates than the linear scan units.

All of the known systems described above offer the advantages of a wider dynamic range than is available with film-based radiography and a reduction in the level of scattered radiation detected after passing through the target. Linear scanning units, however, have limited spatial resolution and relatively slow scan times (on the order of 4 seconds). Image quality can be severely affected by patient motion during the relatively long scanning times required. For many radiographic applications, e.g., chest scans, scoleosis, or fractures, high resolution is not necessary. In addition, in such units scan uniformity problems may exist since the X-ray scanning slits and detectors are "stepped" past the patient (rather than moved continuously). Similar restrictions apply to the imaging capabilities of a spot scanning system. Although the rotating multi-slit concentric cone concept should not encounter scan motion uniformity problems and technically should be capable of multiple frame per second scan rates, such a system will require a permanent installation and have high construction costs for the rotating cones and the fiberoptic minifiber detector arrays proposed. The physical size and expense of such a device makes wide-spread acceptance in a general clinical setting prohibitive.

In passing, reference is made to U.S. Pat. Nos. 2,730,566, 4,315,146 and 4,398,302, which illustrate the prior art arrangements as mentioned hereinabove and which are subject to significant drawbacks.

Accordingly, the principal object of the present invention is to improve subject contrast in X-ray imaging due to scatter effect removal using slit scanning and detecting techniques.

Another object of the present invention is to provide the advantage of the wide dynamic range available from photodiode arrays, along with adequate spatial resolution.

A further object is to provide a system with variable scan times appropriate for many radiographic applications.

Yet another object of the present invention to provide a system adaptable to use in a general clinical setting.

SUMMARY OF THE INVENTION

The present invention, in a broad aspect, is an X-ray emitter source used in conjunction with an apertured scanner and detector system. One disk, with apertures displaced on a radii of the disk, is used to scan and define the X-ray beam impinging upon and penetrating the X-ray target such that each aperture scan describes a unique annulus of the first disk. A second disk, coaxially disposed for synchronous rotation with the first disk, holds corresponding detectors for receiving X-rays passing through the X-ray target.

Each detector consists of an X-ray scintillation phosphor optically coupled to a linear photodiode array. The linear photodiode arrays are readout and the signal digitized and stored in an array processor and computer for image reconstruction.

The rotating scanning system proposed allows both patient and X-ray source to remain stationary. Comparative image quality using standard detector technology can be made variable by manipulating certain aspects of the apparatus, e.g. by employing photodiode arrays coated with various phosphor types in a conventional linear scan format, by varying the speed of the scan, or by varying the configuration of the apertures and detectors.

As a further feature of the invention, the present system is particularly suited for retrofit usage with existing X-ray installations. Thus, the device of the invention with the two synchronously rotating disks may be mounted as a unit for movement into operating association with existing X-ray installations, thus avoiding the need for high cost replacement systems, while enjoying the benefits of the invention.

The objects, features and advantages of the invention will become apparent upon consideration of the following detailed description and the accompanying drawings.

DETAILED DESCRIPTION OF THE INVENTION

Figure 1:
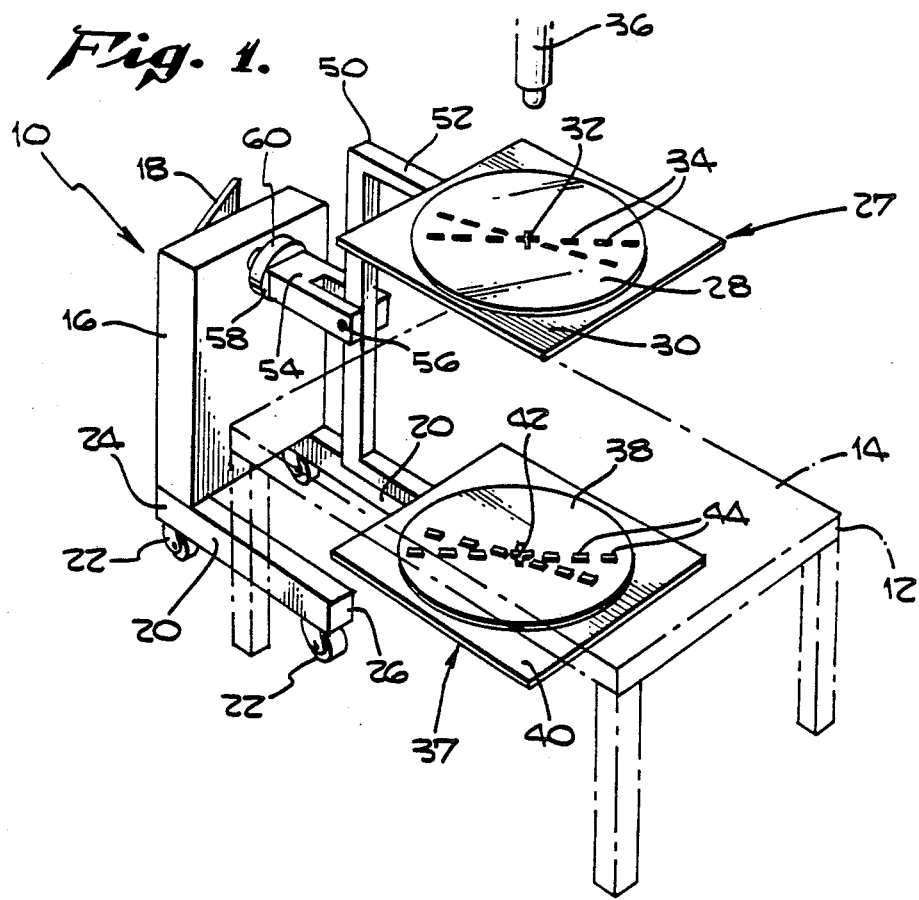
FIG. 1 is a perspective view of the slit scanning and detecting system according to the present invention.

FIG. 1 shows the slit scanning detector system 10 according to the present invention, for radiographic applications such as might be found in any medical X-ray clinic. It is intended that the scanning system 10 be portable. Accordingly, with respect to a common clinic examination table 12, which has an X-ray transparent table top 14, the system 10 is designed with suitable dimensions and construction such that it can be transported readily from one place to another within such a clinic or even between clinics, hospitals, or other technological facilities, and used in conjunction with such a table 12. Likewise, there is provided a housing 16 having an access 18. Housing 16 is mounted upon two transverse leg members 20. Castors 22, or the like, are mounted below the housing 16a at first ends 24 of leg members 20 and beneath the opposite ends 26 of leg members 20, to provide rolling mobility to the system 10.

Figure 6:
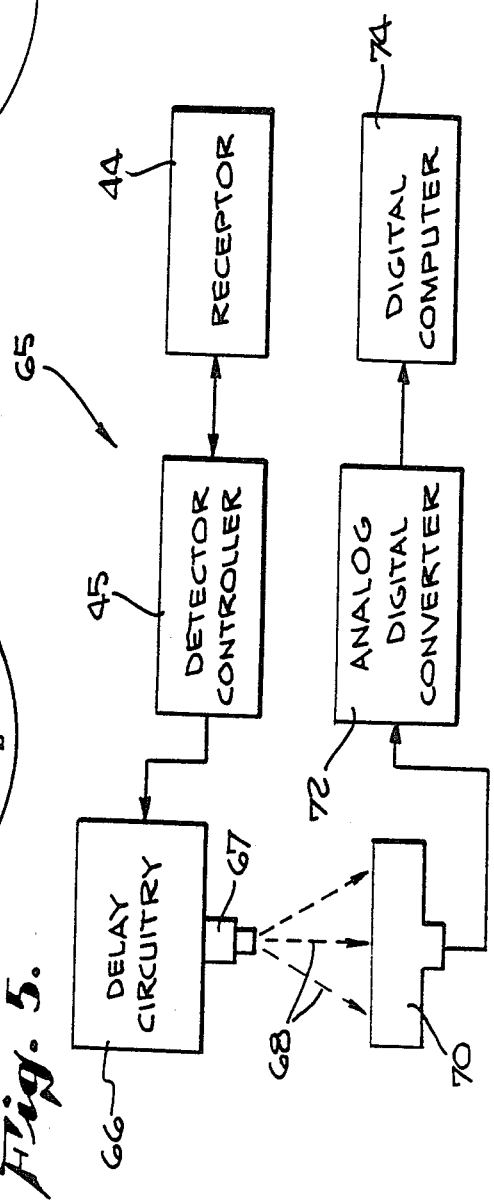
FIG. 6 is a perspective view, partially in cross section, of a segment of the disks shown in FIGS. 3 and 4.

Apertured scanner 27 includes a first rotatable disk 28 constructed of x-radiation opaque material. Disk 28, releasably mounted in a first disk holder 30, is adapted to rotate as a turntable about its center point axis 32. In FIG. 1, an exemplary array of radially extending, discrete apertures 34 is disposed across disk 28. Referring briefly to FIG. 6, a typical aperture slit 34 is shown in a cut-away cross section of disk 28.

Similarly, detector 37 includes a second rotatable disk 38. Disk 38, releasably mounted in a second disk holder 40, is adapted to rotate as a turntable about its center point axis 42. An exemplary array of radially extending, discrete X-ray receptors 44 are disposed on said second disk 38. Receptors 44 can be mounted on the surface of disk 38 or embedded in the surface of disk 38 to present a flush surface.

Figure 2:
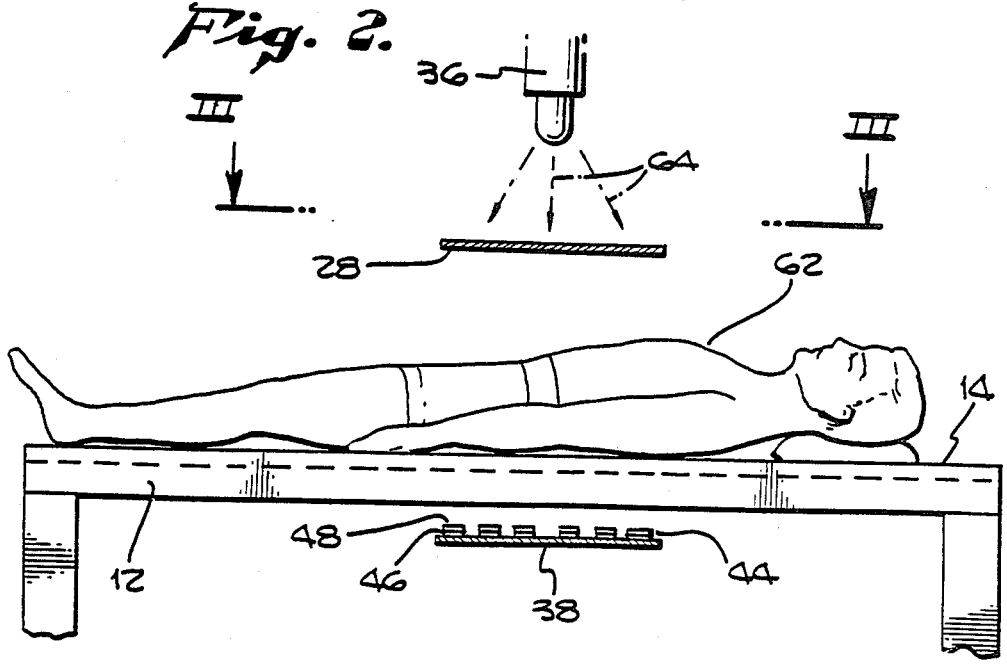
FIG. 2 is a simplified side view of the invention as shown in FIG. 1 showing the orientation of the scanning and detecting system with respect to a target patient.

As shown in FIG. 2, said receptors 44 on second disk 38 typically comprise photodiodes 46 with phosphor coating 48 optically coupled to communicate with said photodiodes. An X-ray sensitive phosphor, which scintillates upon bombardment by X-radiation, is employed. For example, large area linear photodiode arrays, such as RETICON (TM) C-series solid-state line scanners, manufactured by EG&G RETICON Corporation, can be optically coupled to X-ray phosphor 48 by applying a thin film of sodium-silicate as a bond between phosphor 48 and the light sensitive surface of a photodiode array 46. Using a direct application technique, such as a direct spin-gluing application, increases the optical coupling efficiency and improves resolution of the system. X-ray phosphors such as CsI:Tl may be deposited use vapor deposition techniques. Alternatively, conventional fiber-optic coupling between phosphor 48 and photodiode 46 may be employed. However, the technique of direct coupling of an X-ray phosphor material to a photodiode is preferred as it removes the dependence of signal detection upon signal amplification.

The type of phosphor material employed is variable. X-ray phosphors $Gd_2O_2S:Tb,:Eu$ would have a prohibitively long phosphorescent decay time for high speed scanning. CsI:Tl has a shorter decay time which makes it acceptable for imaging rates of 1 frame per second. $CdWO_4$ and BGO have very low after-glow properties but have an X-radiation to visible radiation conversion efficiency of about only one-half to one-third that of $GD_2O_2:Tb,:Eu$. The spectral output for BGO is a noticeably poorer match to the peak sensitivity range for common silicon photodiode arrays than that of $Gd_2O_2S:Tb,:Eu$. However, the conversion efficiency drawback can be offset by the optical coupling gains achieved by employing spin-gluing coupling between the phosphor and the photodetector. Variations can be used to adapt the system to different applications.

Figure 3:
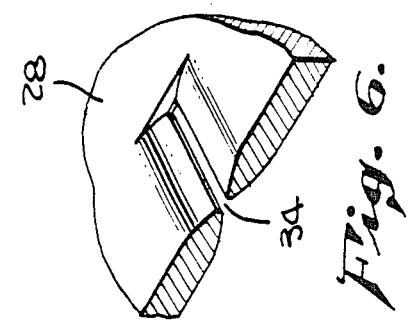
FIG. 3 is a plan view of the disk aperture pattern or photodiode array of FIG. 2 taken through the plane III—III.
Figure 4:
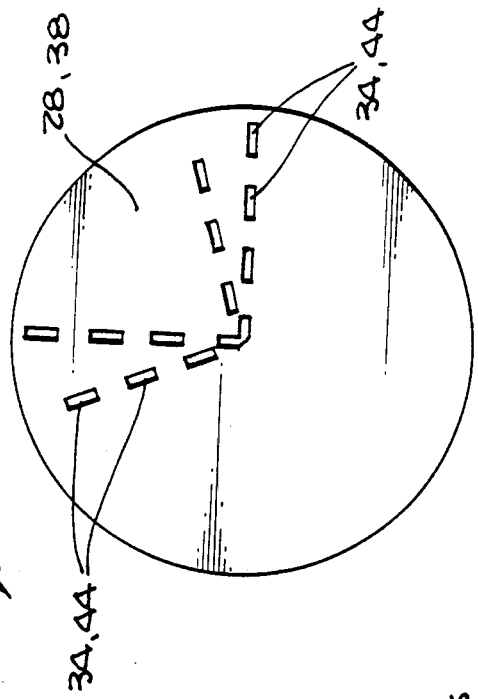
FIG. 4 is a plan view of an alternate embodiment of the aperture pattern or photodiode array of FIG. 2 taken through plane III—III.

Apertures 34 and X-ray receptors 44 are arrayed to define an identical pattern on each of the first and second disks 28, 38, respectively. The pattern can be varied from a single, elongated linear, radial spoke type configuration to multi-element array configurations such as are shown, for example, in FIGS. 3 and 4. With first and second disks 28, 38 mounted in disk holders 30, 40, respectively, disks 28, 38 are oriented in parallel planes and the patterns are aligned with each other radially about and transverse to the axis defined by disk center points 32, 42. Further, as shown in FIG. 2, disks 28, 38 are oriented in order that first disk 28 is disposed between X-ray emitter 36 and an X-ray target (for example, patient 62), and second disk 38 is disposed on the opposite side of the X-ray target 62 from first disk 28. The parallel plane orientation is maintained between disk holders 30, 40 by assembly 50 which pivotally mounts disks 28, 38 and their respective holders 30, 40 to housing 16.

Assembly 50 comprises a rigid U-shaped member 52 which supports disk holders 30, 40 in parallel planes. U-shaped member 52 can be hollow or otherwise adapted to carry any of the conventional apparatus necessary to impart rotational forces to disks 28, 38. Arm 54 has one end 56 rigidly attached to U-shaped member 52 for holding U-shaped member 52, apertured scanner 27, and detector 37 in the predetermined parallel plane spatial orientation. Arm 54 has its other end 58 rigidly attached to a pivot mechanism 60. Pivot mechanism 60 is attached to housing 16 whereby assembly 50 may be rotated at least 90 degrees. Such a rotation of assembly 50 maintains disk holders 30, 40 and their associated disks 28, 38 in parallel plane orientation throughout the arc of rotation of pivot mechanism 60. This allows the system 10 to be used on a patient 62 whether lying prone on clinical table 12 as shown in FIGS. 1 and 2, or on a patient standing between the disk holders 30, 40 upon rotation of assembly 50 about the fixed axis of rotation of pivot mechanism 60.

First disk 28 and second disk 38 are operably disposed for synchronous rotation about the axis defined by their respective center points 32, 42. Being identically patterned, slit 34 array on first disk 28, and photodiode 44 array on second disk 38, remain aligned throughout full rotation cycles of the disks 28, 38.

Various known mechanisms (not shown) can be used as disk drives. For example, a single, variable-speed motor can be operably connected to a central shaft mounted within assembly 50; this shaft could be coupled to disks 28, 38 by belts. Thusly, alignment between the apertures 34 on first disk 28 and their corresponding receptors 44 on second disk 38 during synchronous rotation can be easily effected. Alternatives to this approach could be disk rim drive mechanisms or an induction drive for disk rotation and a feedback system to maintain alignment of the arrays on disks 28, 38. Whatever the means employed, the important aspect is to rotate the disks 28, 38 in synchronicity in order that the annular X-ray beams transmitted by slits 34 on disk 28 are received by the corresponding receptors 44 on disk 38. Housing 16 can be used to contain the mechanism selected for imparting rotation to the disks 28, 38.

Figure 5:
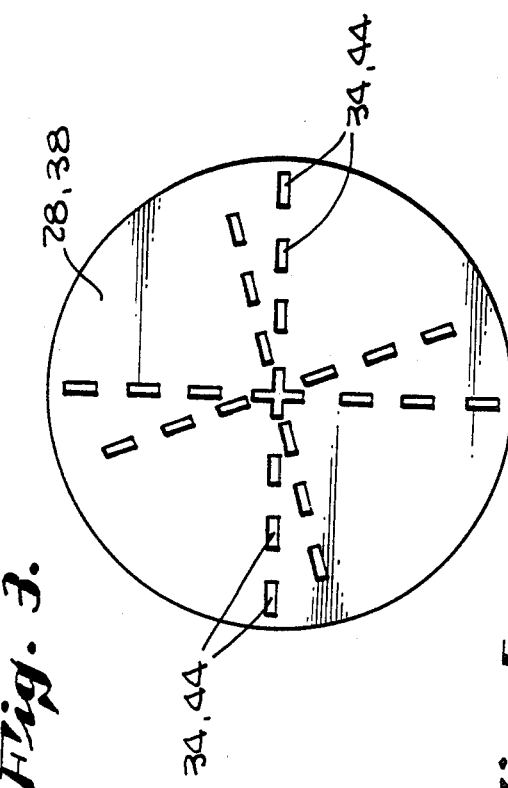
FIG. 5 is a block diagram of the system for processing the output of the detector disk of FIG. 1.

Operation of the slit scanning detector system 10 is best understood with reference to FIGS. 1, 2 and 5. The system can be rolled on castors 22 to a clinic table 12 where patient 62 is reposed on table top 14. With assembly 50 oriented by pivot mechanism 60 so that disks 28, 38 are parallel to the table top 14, first disk 28 becomes located above patient 62 on table 12 between X-ray emitter 36 and patient 62; second disk 38 becomes located below patient 62 and table 12 (X-ray emitter 36 can be integral with or independent of scanning system 10).

Next the disks 28, 38 are set into synchronous rotation; use of a variable-speed disk drive mechanism provides one method for adjusting the desired resolution of the image to be created by the system 10. Upon activation of X-ray emitting means 36, X-rays 46 impinge upon X-radiation opaque, rotating disk 28. The slit 34 aperture array in disk 28 sweeps the impinging X-ray beam 46 such that each slit 34 scans a unique annulus of the disk 28. Hence, the X-rays passing through said slits 34 project a series of annular beams onto patient 62. Briefly referring to FIGS. 3 and 4, an eighteen inch diameter disk, for example, may accomodate a 7 inch scan radius sweeping out a 14 inch scan of patient 62. By precisely staggering the array pattern along two or more radii, a discrete series of annular beams projected by disk 28 forms a continous set of ring beams on the patient 62. X-rays passing through patient 62 and table top 14 impinge upon the X-ray scintillating phosphors 48 of receptors 44. Receptors 44 array pattern being identical to aperture 34 array pattern and disks 28, 38 being aligned in parallel planes and moving in synchronicity results in each annular X-ray beam projected by the slits 34 and passing through patient 62 being continously received by a corresponding receptor 44.

The X-ray scintillating phosphor 48 energized by the impinging X-rays phosphoresce. Each phosphor 48 being optically coupled to photodiode 46 array, said array detects the light output from the X-ray sensitive phosphor 48. In practice, the physical size of each photodiode array chip 46 dictates the positioning of the X-ray aperture slits 34 and detector 44 arrays in the above said staggered pattern about the radii of their corresponding disks 28, 38; successive detector 44 arrays sample from successive X-ray annuli swept out by apertures 34.

Having detected the X-rays 46 passing through the patient 62 with receptors 44, the system requires a device to process the received information. Said processor 65 can be comprised of commercially available data retrieval and processing equipment which operates as follows.

The linear photodiode 46 arrays will detect the phosphorescent light output from the X-ray sensitive phosphor 48. All arrays are scanned and readout simultaneously by individual controller boards at repeated time intervals while the disks 28, 38 rotate. A master clock initiates all scans simultaneously but the output data from each receptor 44 of the array is appropriately delayed with respect to its distance from the center of disk 38, then transmitted 68, using a standard optically coupled transmitter 67 to a stationary receive 70. The signal will then be digitized in a conventional analog-to-digital converter 72 and stored in a memory bank or immediately transmitted to a computer 74 for permanent storage or to a dedicated array processor complex memory used for general image reconstruction.

Each linear slit 34 array essentially sweeps out an annulus of a disk which can be recombined with other annuli to form an image. The final imaging involves reconstructing individual pixel elements. Since the receptor 44 element at the center of the disk 38 remains stationary, it can be monitored for variations in X-ray emitter 36 output, such as ripple.

The power required to operate the receptor 44 arrays and associated electronics can be provided by a multiple contact-brush system, which is known to greatly reduce the noise and power irregularity problems associated with single brush systems. An alternative power source might comprise the incorporation of high output batteries (since real power demands are greatly reduced by the short scan times involved-approximately one second). The power source can be operably mounted in housing 16.

Operation of the scanning and detecting system 27, 37 and an integral X-ray source can be microprocessor controlled. The rotating disk format allows patient 62 and X-ray source 36 to remain stationary, also allowing shorter scan times without loss of resolution. Depending on the desired spatial resolution (resolution will, of course, vary from center to edge since the beam arcs form rectangular pixels), if the X-ray source is operated in a pulsed mode rather than continously, degradation of edge resolution as distance from the center of the disk increases can be partially compensated for by modifying the initial radial placement of the detectors. Furthermore, the ability of the system to increase image pixel size by either increasing scan interval times or electronically merging data can be used to reduce patient dose when lower spatial resolution is adequate. Rotational slit scanning as disclosed herein will reduce scatter detection while providing frame rates sufficient for general radiographic, and possibly angiographic, applications.

The references cited in the Background of the Invention section of the present invention will now be considered in greater detail.

Initially, consideration will be given to Pfeiler, U.S. Pat. No. 4,398,302, granted Aug. 9, 1983. The Pfeiler patent appears to be of the type involving a dedicated apparatus in which the X-ray tube rotates along with a slotted rectangular member. The X-ray tube is rotated because this patent is based on the idea that uniformity is necessary. Unfortunately, this uniformity is only obtained for a constant-thickness phantom. A real patient is not uniform over many regions and therefore nonuniform radiating sources can be used to advantage. Moreover, at this time, there is no general radiographic tube that does not exhibit the so called "heel" effect involving preferential beam "hardening" or higher intensity radiation in certain patterns. Our system is compatible with these general radiographic principles and constraints. Clearly, a conventional tube can be used only with the prior patent to Pfeiler if the tube actually rotates. However, there are two conceptual differences which are believed to be involved with the configuration of the prior patent to Pfeiler and which make it inferior to fixed X-ray tube installations:

1. Uniformity is required over the entire imaging area. This assumption is correct, but uniformity in a study, such as a chest scan, is often obtained by a feedback circuit which increases the tube current as a thick part of the chest is imaged because increased X-ray output is needed to provide the same output statistics for thicker parts of the chest. A uniform beam is not always necessary, however. The physician often positions a patient so that a thicker or denser part of the patient is along the direction of the harder part of the beam. In laymen terms and in a practical way, the skilled radiologist will line up the more intense or concentrated part of the X-ray beam with the patient's sternum or breastbone, which is the thickest part of a human chest. Thus, uniformity can be improved by a simple patient positioning relative to the fixed X-ray tube; and this would of course not be possible with the rotating tube arrangements of the Pfeiler patent.

2. Uniformity can be obtained by using a particular tube emission direction (i.e., aligning the slit to obtain a uniform beam). Uniformity could also be obtained by using a shaped filter which is designed according to the emission characteristics of the focal spot. Of course, Pfeiler uses neither of these techniques.

The device of the present invention is, of course, consistent with the utilization of non-uniform beams, and therefore represents a significant advance as compared with the device disclosed in the Pfeiler patent. Incidentally, with regard to the Pfeiler system, there is no teaching whatsoever that anything except a rectangular member could be employed, with this member rotating along with the X-ray tube.

Furthermore, the Pfeiler invention is not readily adaptable to preexisting X-ray units set up in hospitals and in clinics throughout the nation. In contrast, the present invention is portable and retrofits onto existing X-ray installations. In addition, the present invention is not as expensive as the massive arrangement disclosed by the Pfeiler patent. Because of the present invention's portability, it can be removed when there are no operators skilled in its usage. It is also noted that the system of Pfeiler involves a complete dedicated X-ray system, and could not be used with existing X-ray equipment.

Now attention will be directed to Bartow, U.S. Pat. No. 2,730,566, granted Jan. 10, 1956. The Bartow patent discloses a radiopaque disc, a radiographic target, and a second aperture disc. Apparently, the image area constitutes a very small portion of the area of the discs. The Bartow patent also discloses a single detector which detects radiation which passes through any of the apertures of the second aperture disc. This arrangement would appear to provide very poor resolution because the arrangement of apertures would appear to involve in some case two apertures being sensed by one amplifying arrangement at the same time. This would, of course, have the undesirable effect of having signals from two separate apertures passing through two portions of a material, being imaged simultaneously. This effect would give a false reading at the output from the amplifying arrangement. Moreover, the Bartow arrangement would appear to provide very slow scanning, as each point on the final image would necessarily have to be processed through the one amplifying arrangement. In all events, with only one amplifying arrangement, providing the signal for each one of the points on the final image, it is clear that either the resolution would be very poor, or else that the required time for providing a picture would be exceedingly long, thereby exposing the patient to a substantial level of radiation. In contrast, using the arrangement of the present invention, the detecting rays are aligned with the slit apertures and thus the higher resolution and more rapid processing is practical.

Now, considering Rudin, U.S. Pat. No. 4,315,146, this patent discloses an apparatus for reducing the radiation scatter in forming images of internal structures upon a sensing means such as fixed conventional X-ray film. The radiation scattering is reduced by passing a portion of the radiation beam through apertures of rotating radiopaque shields, one such shield being between the radiation source and the object, and another shield being located between the object and the detection means. Accordingly, the Rudin patent discloses a broad area dector rather than the narrow detector disclosed here, which are synchronized with the openings of the radiopaque aperture disc. When such a broad area detector is used, as in the Rudin patent, each area of the image will be blurred by scattering during the entire time the X-ray tube is energized, whereas in accordance with one aspect of the present invention, a clearer image is obtained by detecting only directly transmitted radiation. In addition, according to FIG. 1 of the Rudin patent, the apparatus appears to be a massive permanent installation. This is contrary to the present invention which is portable and easily adaptable to be retrofitted to the existing X-ray installations.

In the foregoing description of the present invention, a preferred embodiment of the invention has been disclosed. It is to be understood that other design variations are within the scope of the present invention.

What is claimed is:

1. A movable X-ray device having a wide dynamic range, for use with existing X-Ray installations, including means for emitting an X-Ray beam fixed to and forming part of the fixed existing X-Ray installation, comprising:

radiopaque apertured disk means having a plurality of at least four separate radially extending interrupted slits, each said radially extending slit extending over a predetermined radial distance, and the entire plurality of said radially extending slits encompassing each radial distance from the center of said disk to a maximum radius near the periphery of said disk;

solid state receptor means mounted on a second disk, said receptor means being aligned with the respective slits in said radiopaque disk means, said receptor means including a plurality of spaced individual receptor assemblies aligned, respectively, with said slits;

means for rotating said radiopaque disk and said second disk synchronously and coaxially with said fixed X-Ray source adjacent said radiopaque disk, and a radiographic target between said two disks; and means for mounting (1) said radiopaque disk means, (2) said solid state receptor means and said second disk, and (3) said means for synchronously rotating said radiopaque disk and said second disk, all in a single movable assembly as a unit, for movement toward and away from existing X-Ray installations, which existing installations include the fixed means for emitting an X-Ray beam;

so that said movable device may be selectively employed with existing X-Ray installations.

2. A device as defined in claim 1 wherein said receptor means comprises:

photodetector means; and

X-ray scintillation phosphor coating disposed in optical communication with said photodetector means.

3. The device as defined in claim 1 wherein said device further comprises:

variable speed means for controlling the speed of rotation of said first and second disk means.

4. A device as defined in claim 1, wherein said device further comprises:

X-ray image recording means; and electrical interface means for connecting said receptor means to said recording means to transmit annularly-shaped X-ray scans from said receptor means to said recording means.

5. A device as defined in claim 4, wherein said recording means comprises:

digital computer means for analyzing said X-ray scans after passage through said target and reception by said receptor means.

6. A device as defined in claim 5, wherein said electrical interface means comprises:

detector controller means, coupled to said receptor means, for controlling the operation of said receptorr means, electro-optical means, coupled to the output of said detector controller means, for transmitting the signals generated by said receptor means; and analog-to-digital converter means, coupled to the output of said electro-optical means, for digitizing the information to be supplied to said digital computer means, whereby said annularly-shaped X-ray scans can be recorded and analyzed.

7. A device as defined in claim 1, wherein said device includes means for mounting and rotating said radiopaque disk and said second disk at the edge of each said dish.

8. A slit scanning device for use with existing radiological systems including a stationary X-Ray emitting source forming part of the existing radiological system, comprising:

first rotatable disk means, disposed between said X-ray emitting source and an X-ray target and defining a radially disposed slit aperture array including a plurality of at least six radially extending interrupted slits for producing a plurality of annularly shaped X-ray scans of said target;

second rotatable disk means, disposed coaxially with said first rotatable disk means and on the opposite side of the target from said first rotatable disk means;

a plurality of individual radially arrayed X-ray receptor means, disposed upon said second rotatable disk means in alignment with said aperture array, for detecting said X-ray scans after penetration of said target, said receptor means including a plurality of spaced individual receptor assemblies aligned, respectively, with said slits;

means for rotating said first and second disk means in synchronism, with X-rays from said source passing through the slits of said array and impinging on said individual receptor means; and means including rollers for mounting (1) said first disk means, (2) said second disk, and said receptor means and (3) said means for rotating said first disk and said second disk, all in a single movable assembly as a unit, for movement toward and away from existing X-ray installations;

so that said movable device may be selectively employed with existing X-ray installations.

9. A device as defined in claim 8, wherein said receptor means comprises:

photodetector means; and

X-ray scintillation phosphor coating disposed in optical communication with said photodetector means.

10. The device as defined in claim 8, wherein said device further comprises:

variable speed means for controlling the speed of rotation of said first and second disk means;

X-ray image recording means; and electrical interface means for connecting said receptor means to said recording means, to transmit annularly-shaped X-ray scans from said receptor means to said recording means.

11. A device as defined in claim 10, wherein said recording means comprises:

digital computer means for analyzing said X-ray scans after passage through said target and reception by said receptor means.

12. A device as defined in claim 10, wherein said electrical interface means comprises:

detector controller means, coupled to said receptor means, for controlling the operation of said receptor means;

electro-optical means, coupled to the output of said detector controller means, for transmitting the signals generated by said receptor means; and analog-to-digital converter means, coupled to the output of said electro-optical means, for digitizing the information to be supplied to said digital computer means, whereby said annularly-shaped X-ray scans can be recorded and analyzed.

13. A device as defined in claim 8, wherein said device includes means for mounting and rotating said radiopaque disk and said second disk at the edge of each said dish.

14. A movable X-ray device having a wide dynamic range, for use with existing X-ray installations, including means for emitting an X-ray beam, fixed to and associated with the existing X-ray installation, comprising:

radiopaque apertured disk means having a plurality of at least five separate radially extending slits, said slits being interrupted and overlapping to provide at least one slit having an opening at each radial distance;

solid state receptor means mounted on a second disk, said receptor means being aligned with the respective slits in said radiopaque disk means, said receptor means including a plurality of spaced individual receptor assemblies aligned, respectively, with said slits; and means for rotating said radiopaque disk and said second disk synchronously and coaxially, with said fixed X-ray source adjacent said radiopaque disk, a radiographic target between said two disks; and means for mounting (1) said radiopaque disk means, (2) said receptor means and said second disk, and (3) said means for rotating said radiopaque disk and said second disk, all in a single movable assembly as a unit, for movement toward and away from existing X-ray installations which existing installations include the fixed means for emitting an X-Ray beam;

so that said movable device may be selectively employed with existing X-ray installations.

15. A device as defined in claim 14, wherein said receptor means comprises:

photodetector means; and

X-ray scintillation phosphor coating disposed in optical communication with said photodetector means;

X-ray image recording means; and electrical interface means for connecting said receptor means to said recording means, to transmit annularly-shaped X-ray scans from said receptor means to said recording means.

16. A device as defined in claim 15, wherein:

said recording means comprises:

digital computer means for analyzing said X-ray scans after passage through said target and reception by said receptor means;

said electrical interface means comprises:

detector controller means, coupled to said receptor means, for controlling the operation of said receptor means;

electro-optical means, coupled to the output of said detector controller means, for transmitting the signals generated by said receptor means; and analog-to-digital converter means, coupled to the output of said electro-optical means, for digitizing the information to be supplied to said digital computer means, whereby said annularly-shaped X-ray scans can be recorded and analyzed.

17. A device as defined in claim 14 wherein individual separate solid state receptor array means are mounted on said second disk in alignment with each separate slit.

18. A device as defined in claim 14, wherein said device includes means for obtaining X-ray image information from substantially the entire cylindrical volume between said two rotating disks and extending outwardly to the extent of the outermost of said slits.

19. A movable X-Ray device having a wide dynamic range, for use with existing X-Ray installations, including X-ray source means for emitting X-Ray radiation fixed to and forming part of the existing installation, comprising:

radiopaque apertured disk means having a plurality of at least eight separate radially extending interrupted slits, each said radially extending slits extending over a predetermined radial distance, and the entire plurality of said radially extending slits encompassing each radial distance from the center of said disk to a maximum radius near the periphery of said disk;

solid state receptor means mounted on a second disk, said receptor means being aligned with the respective slits in said radiopaque disk means, said receptor means including a plurality of spaced individual receptor assemblies aligned, respectively, with said slits;

means for rotating said radiopaque disk and said second disk synchronously and coaxially, with said fixed X-Ray source means adjacent said radiopaque disk, and a radiographic target between said two disks;

said X-ray device including means for mounting said disks substantially concentrically relative to the X-Ray source means so that X-ray radiation may be directed through the entire surface of each of said disks; and means for moving said two disks and said means for rotating them into and out of operational proximity to existing X-Ray installations, which existing installations include the fixed means for emitting an X-Ray beam.

20. A device as defined in claim 19, wherein said device includes means for mounting and rotating said radiopaque disk and said second disk at the edge of each said disk.

* * * * *

UNITED STATES PATENT AND TRADEMARK OFFICE
CERTIFICATE OF CORRECTION

PATENT NO. : 4,763,345
DATED : August 9, 1988
INVENTOR(S) : Barbaric et al

It is certified that error appears in the above-identified patent and that said Letters Patent is hereby corrected as shown below:

The title of the invention should read --Slit Scanning And Detecting System--.

Signed and Sealed this

Tenth Day of January, 1989

*Attest:*

DONALD J. QUIGG

*Attesting Officer*     *Commissioner of Patents and Trademarks*